United States Patent [19]

Izzo et al.

[11] 4,230,693

[45] Oct. 28, 1980

[54] ANTACID TABLETS AND PROCESSES FOR THEIR PREPARATION

[75] Inventors: Henry J. Izzo, Naperville; Martin J. Moran, Oak Lawn, both of Ill.; Frederick G. Wheeler, Poplarville, Miss.

[73] Assignee: Armour-Dial, Inc., Phoenix, Ariz.

[21] Appl. No.: 747,172

[22] Filed: Dec. 3, 1976

Related U.S. Application Data

[63] Continuation of Ser. No. 569,947, Apr. 21, 1975, abandoned.

[51] Int. Cl.³ .................. A61K 33/10; A61K 33/08
[52] U.S. Cl. .................................. 424/156; 424/157
[58] Field of Search ............... 424/157, 156; 264/109, 264/115, 122

[56] References Cited

U.S. PATENT DOCUMENTS

| | | | |
|---|---|---|---|
| 1,889,366 | 11/1932 | McGowan | 264/109 |
| 3,253,988 | 5/1966 | Scott | 424/157 |
| 3,843,778 | 10/1974 | Diamond et al. | 424/157 |

OTHER PUBLICATIONS

Remington's Pharmaceutical Sciences, 13th Ed., (1965), pp. 562–584.

*Primary Examiner*—Frederick E. Waddell
*Attorney, Agent, or Firm*—Frank T. Barber; Carl C. Batz; Richard G. Harrer

[57] ABSTRACT

An antacid tablet is prepared which contains a combination of an antacid ingredient, sugar, and fat and which has a hardness requiring no more than 9 pounds peak force to cause a blunt probe to penetrate its surface. Included also are processes for preparing such a tablet in which an antacid ingredient, sugar, and melted fat are mixed, cooled and milled to produce a powdered mixture, and the mixture formed into tablets. Further improvements include using a fine sugar, 90% of which will pass a 200 mesh screen; maintaining the plungers and dies of the tableting machine above the melting point of the fat; and utilizing a limited pressure (50 to 600 pounds per square inch) in the compressing of the tablets. Another feature involves controlling the moisture to within 3 to 10% based on the weight of the tablet.

5 Claims, No Drawings

ANTACID TABLETS AND PROCESSES FOR THEIR PREPARATION

This is a continuation of U.S. patent application Ser. No. 569,947 filed Apr. 21, 1975, now abandoned.

This invention relates to antacid tablets and to processes for their preparation. More particularly, the invention deals with such tablets containing the combination of an antacid ingredient, sugar and a high proportion of fat.

BACKGROUND

Antacid compositions have been prepared in a wide variety of forms such as suspensions, solutions, emulsions, powders and tablets. In each case the composition includes an ingredient which is an effective antacid substance and such substances include calcium carbonate, magnesium carbonate, magnesium hydroxide, magnesium trisilicate, magnesium oxide, sodium bicarbonate, aluminum hydroxide, aluminum carbonate, aluminum hydroxycarbonate, aluminum magnesium glycinate, dihydroxy aluminum amino acetate, and magnesium aluminate. Many other compounds also come to be useful as antacid ingredients in compositions of this type. One such ingredient is aluminum hydroxide-magnesium carbonate composition which is prepared as a dry gel by Reheis Chemical Company and sold under the code name FMA-40. Another such composition having somewhat different proportions of the same ingredients is sold under the trade code FMA-11. In the specification and claims we use the term "antacid ingredient" to mean any of the above-mentioned antacid substances and mixtures thereof, together with any compounds which include any of the above as a part of a chemical complex.

Antacid compositions containing the antacid ingredients above referred to may be more effective when made up in solutions or suspensions because liquid medication can more easily reach the affected areas where treatment is needed whereas in the case of powders or tablets, these do not break up into the fine particle size of liquid suspensions and some of the medication may never reach the areas where treatment is needed. This is true especially as to tablets which require mastication in the mouth. In some cases antacid tablets or portions of them may even pass into the body in solid form without giving up any substantial medical benefit. Also, antacids in tablet form are as a general rule slower to take effect and slower to give relief from symptoms of hyperacidity than if the same medicaments were contained in the form of solutions or suspensions.

However, the tablet form of antacid medication is much more convenient to the patient. The tablets may be carried in small containers or in a purse and may be taken as needed without any need for extra equipment or for the measuring of dosages. Despite limitations in giving relief, the convenience of the tablet form of the antacid make this form a popular kind of antacid composition.

What has been needed is an antacid tablet which is more effective in giving relief to symptoms of hyperacidity, a tablet which will release its benefits more rapidly, which will pass easily to the areas where treatment is needed, and which will also yield benefits to the patient over a longer period of time. At the same time it is desirable that the ingestion of the tablet be pleasant and without discomfort to the patient such as would be caused by grittiness or other unpleasant feeling in the patient's mouth.

Accordingly, Applicants have set out to discover an improved antacid tablet which will meet the needs above expressed.

Applicants conceived the idea that an improved tablet containing fat in combination with an antacid ingredient and sugar, the fat being contained in a relatively high proportion in the tablet; also that the tablet have a very limited hardness; but according to the prior teachings and the prior practice in the tableting art, such a tablet could not be prepared. For one thing, a material having such a high proportion of fat along with sugar and antacid would be expected to stick to the cavity walls and to the punches of the tableting presses so that the tablets could not be ejected from the press.

Accordingly, Applicants set out to provide a process for preparing the improved antacid tablets which avoids the difficulties facing the art, a process by which the tablets may be made with ease.

SUMMARY

The improved antacid tablets of this invention contain the antacid ingredient, sugar, a small amount of moisture, and an appreciable quantity of fat. The invention further involves a process in which the tableting machine, including the punch elements of the presses, are maintained at an elevated temperature. Yet another feature involved in the process is that of controlling the pressure which is applied in the tableting operation. Other features involve the particular characteristics of the ingredients utilized in preparing the tablet, and in their manipulation in the course of manufacture.

We are aware that each of the antacid ingredients, the sugar, and the fat have separately been formed into tablets, but believe that their combination in accordance with disclosures herein contained constitutes a basic improvement in this art.

DETAILED DESCRIPTION

As the antacid ingredient we may use any of the substances which have been used in the prior practice in making antacid compositions including any of those which we have mentioned above under "Background" but we prefer combinations of aluminum hydroxide, magnesium oxide and magnesium carbonates, particularly that combination sold under the trade code FMA-40. Such substances may be in the form of a fine powder, the size of the particles in terms of density being something of the order of 0.15 grams per millimeter plus or minus 0.1 grams.

As the sugar ingredient we prefer to use sucrose. We may use also dextrose, lactose, fructose, galactose, manitol, sorbitol, maltose or sugars of other particular types. It is possible that the dextrose and other sugars, other than sucrose, may give some difficulty by browning. We prefer also that the sugar be in the form of fine powder sometimes called "fondant sugar" which is of a fineness such that at least 50% will pass through a 200 mesh screen. It is better that at least 90% of the sugar pass through a 200 mesh screen. This sugar ingredient may contain a small amount of a material such as starch in the form of cornstarch or tapioca—we prefer pregelatinized tapioca—as an anticaking agent in the amount of about 2.9% of the weight of the finished tablet.

As the fat ingredient we may use any natural or synthetic fat such as animal or vegetable fats and shortenings. We prefer that the fat have a melting point not higher than 115° F., and find that fat having a melting point of the order of 101° to 103° F. is most useful.

In addition to the antacid, sugar and fat ingredients, we may add a suitable dye to provide a desired color, common salt and a flavoring agent to provide a desired flavor, and water as needed in the processing. All materials should be of pharmaceutically acceptable quality.

To combine the ingredients, we may put a quantity of water, for example about 25 liters, into a suitable mixing container, and add the dye and salt in a water solution and mix to attain a complete solution. Water may be added to give the desired amount of water, for example, about 27 liters, mixing thoroughly.

The sugar, containing a small amount of an anticaking agent, may be placed in a mixer, the mixer started and the dye solution added slowly, mixing for a few minutes until the batch has a creamy consistency and uniform color.

The improved antacid tablets prepared in accordance with our invention may contain the following percentages of essential ingredients:

| Ingredient | Usable Percentage | Preferred Percentage |
| --- | --- | --- |
| Antacid | 5 to 40 | 12 to 30 |
| Sugar | 15 to 80 | 35 to 65 |
| Starch | 0 to 6 | 1 to 5 |
| Fat | 3 to 40 | 15 to 30 |
| Water | 2 to 12 | 4.5 to 9 |

The percentage values of ingredients above given are by weight based on the weight of the tablets which are prepared.

From the above information as to the primary constituents of the finished tablets, specific amounts of the ingredients may be selected from the ranges given and the amount of the respective antacid, sugar and fat starting materials may be calculated to make the desired proportions in the finished tablets.

The fat may be heated to a temperature above the melting point of the fat, of the order of 120° to 130° F. (49° to 54° C.) to change the fat to a liquid, and the flavoring agent may then be mixed in.

Then the melted fat having the flavoring therein and the powdered antacid ingredient may be thoroughly mixed to produce a uniform dispersion of antacid throughout the fat. The water, coloring and salt are thoroughly mixed with the sugar to form a fondant-like mixture. These two separate mixes may then be blended until they are completely dispersed in each other. Any powdered flavoring agent which it is desired to use may also be mixed in at this point. The batch is now ready for granulation.

The batch in the mixer may be cooled as it is being mixed by the addition of dry ice until the temperature of the batch has dropped to something below 40° F., for example, to about 35° to 40° F. (2° to 4° C.).

The hammermill, one type of which is known as a Fitzmill, may be prepared by passing dry ice through it while operating at high speed with impact forward.

The cooled batch may then be passed through the hammermill operating at high speed with impact forward. The cooled temperature may be maintained by the introduction of a coolant such as liquid nitrogen. Preferably the temperature of the batch as it comes from the hammer is near or below 0° C. The temperature may be substantially below 0° C., there being no limit on the lower side except that when the temperature is very low, heat is required to bring it back to the temperature at which continued processing can take place.

The material from the hammermill may be put into a dryer and dried at a temperature, for example, of about 70° to 75° F. The moisture may be brought down at this point to about 8 to 10% based on the weight of the material. Then we prefer to pass the dried material through an agglomerator to make a more uniform size of particles. We prefer that the operation be continued until all of it will pass through a 4 mesh screen so that a maximum of 15% will pass a 40 mesh screen. If desired, the agglomerated material may be further dried to as low as 3% moisture, desirably in the range of about 6.8 to 7.8% based on the weight of the material has proved to be quite satisfactory.

The foregoing detailed description of the preparation of material for tableting sets forth what Applicants believe to be the best procedure but it will be apparent that this procedure may be abbreviated by omission of non-essential steps. For example, the flavoring and dye ingredients may or may not be included and the material prepared using only the essential antacid ingredient, the sugar and the fat along with a small amount of moisture. Also, the various detailed steps may be varied or changed in many respects in accordance with the knowledge of the art.

The proportions of the antacid ingredient, the sugar and the fat may also vary. The improved tablet may contain from 5 to 40% antacid ingredient, from 3 to 40% fat, from 15 to 80% sugar, with the preferred fat range being from 15 to 30% and water in the proportion of from 2 to 12% with from 4.5 to 9% preferred. Pregelatinized tapioca starch may be included in the preferred range of 1 to 5%. All of the above percentages are weight amounts based on the total weight of the mixture after drying. The quantities of these ingredients for any particular batch may be determined as required to result in the selected proportion of ingredients, the size of the batch, etc.

The antacid powder composition prepared as above described may be compressed into tablets of desired form using a standard tableting machine by operating the machine in a prescribed way. It is important first that the tableting machine, or at least those parts of the machine which contact the tablets under compression, be maintained at a temperature at or above the melting point of the fat contained in the tablets. This may be done by heating the room in which the tableting operation is performed to an elevated temperature above normal room temperature and above the melting point of the fat, suitably about 110° to 125° F. (43° to 51° C.), or by enclosing the tableting machine in a shroud and maintaining the temperature within the shroud at the elevated temperature just referred to. The dies and punches of the press are maintained at a temperature which keeps the fat liquid at the punch/tablet interface and allows the tablets to come off the tableting machine without sticking. This may be accomplished by the use of lamps which direct infrared light toward the machine. If the temperature of the punches on the tableting machine is below the melting point of the fat, then the fat which melts at the interface on compression solidifies before the tablet is released, causing sticking of the tablet to the punches.

It is also important to limit the pressure used in forming the tablets. The pressures commonly used in tableting are of the order of 2000 or 3000 pounds per square inch, but we find it advantageous in forming our improved antacid tablets to use pressures substantially lower than this and within the range of from about 50 to 600 pounds per square inch, preferably from about 150 to 400 pounds per square inch.

The tablets which are formed using the conditions above described may be collected, packaged and distributed through regular trade channels.

The improved tablets have been found to be very effective in use. We believe this is due in part to the use of fat in the tablets in combination with the antacid ingredient and sugar constituents. This gives the tablets a better eating quality and mouth feeling, and helps to form a coating which lines the esophagus and which resists the effects of stomach acid juices. The fat also helps to densify the active antacid ingredient in the process of manufacture since the fat and antacid are premixed and this permits the whole batch to be more easily mixed in a uniform manner. Further, it is believed that the effect of the fat extends the time during which the tablet gives beneficial effect. Also, the lower values of hardness are believed to contribute to the easy breakup of the tablet in the mouth, and this provides more surface area of antacid material and therefore quicker and more complete action.

The following specific examples demonstrate the practice of our invention in the preparation of the improved antacid tablets:

EXAMPLE I

A dye solution was prepared using the following supplies:

| Constituent | Quantity | Percent |
|---|---|---|
| Dye, FD&C Yellow #5 | 6.38 g | .0226 |
| Dye, FD&C Blue #1 | 2.13 g | .0076 |
| Sodium Chloride USP | 1215. g | 4.3049 |
| Tap water | 27.0 L | 95.6649 |
| Total | 28.225 Kg | 100.00% |

25 liters of filtered tap water was placed in a mixer and the dye solution added to it. Water was added to make 27 liters.

44.65 Kg of powdered sucrose having a fineness such that more than 90% passes a 200 mesh screen and containing 2.6 Kg of pregelatinized tapioca, was placed in a Sigma Day mixer, the mixer started and the dye solution added to the sucrose. Mixing was continued until the batch had a creamy consistency.

22.5 Kg of hydrogenated vegetable fat (having the trade name Duromel) was liquefied by heating to 120° F. 20.0 g of spearmint oil and 35.0 g of peppermint oil were added to the fat and mixed in.

13.5 Kg of FMA-40 were intermixed and added to the Sigma Day mixer. Mixing was continued until the mass became completely uniform. Dry ice was added to keep the batch at a temperature of between 35° and 40° F.

The batch was put through a hammermill operated at high speed with impact forward while introducing liquid nitrogen to maintain the batch temperature at about −10° to −20° F. The temperature of the batch coming from the hammermill was about 0° to −10° C.

The batch was then transferred to a fluid bed drier operated at about 70°-75° F. until the batch came to this same temperature and a moisture of 8 to 8.6%. The batch was then transferred to a blender where agglomeration took place and the agglomerated mass was then classified by passing the same through a No. 4 screen, and then further dried to a moisture content of about 7%.

In the tableting operation we used a tableting machine preheated to 120° F. and a shroud of polyethylene film about the tableting machine and heated the air within the shroud to about 75° to 100° F., and used a pressure on the plungers of the machine of 300 pounds per square inch. We used heating lamps to maintain the machine temperature of from 105° to 120° F.

Then the batch material was fed to the tableting machine and tablets formed. The tablets were collected and packaged in polyethylene-lined cans.

EXAMPLE II 1212 g of dried fondant sugar were blended with 10.5 g of salt and 43 g water containing 15 drops of color and 30 drops of peppermint flavor. 319.05 g of finely powdered antacid material (FMA-11 and FMA-40, each of which is a mixture of aluminum hydroxide and magnesium carbonate) was dispersed in 584.85 g of melted shortening (melting point 102°-105° F.). The two above-described mixtures were blended together and allowed to cool and solidify. The cooled mass was ground in a Fitzpatrick hammermill using liquid nitrogen injected into the milling head as a coolant. The mill was operated at 5800 rpm and the screen through which the material must pass was 0.0156 inches in diameter. The resulting powder was used to make antacid tablets using a compression pressure of 250 pounds per square inch with the machine shrouded by a polyethylene film and the temperature of the machine maintained at 100° to 125° F.

EXAMPLE III 606 g of dried fondant sugar, 60 g of corn syrup, 5.5 g of salt and 25 g of water were mixed together in a Hobart mixer. To this mixture was added gradually 292.5 g of melted shortening having a melting point of 102° to 105° F. To this was added 7 drops of green food coloring and 15 drops of peppermint flavor. Mixing was continued until the mass was uniform. At this point 399 g of FMA-11 was added. This was mixed in thoroughly and the mass allowed to cool and crystallize out. The cooled, crystallized mass was put through a "finishing machine" (a swept screen type of machine in which the material is forced through the screen by revolving blades). The powder from this procedure was tableted as set forth in Example II.

EXAMPLE IV 2 pounds of fondant sugar (fine enough that 90% or more will pass a 200 mesh screen), ¼ oz. of salt, 2½ oz. of water, and 11 drops of green food coloring were mixed together in a Hobart mixer. 8½ oz. of finely powdered antacid mixture (FMA-11) were dispersed in 15½ oz. of melted shortening (102° to 105° F. melting point). The shortening and antacid mixture was added to the Hobart mixer with the sugar mixture, and mixing was continued until a homogenous smooth mass was obtained. The mass was allowed to cool and crystallize out. It was then ground through a hammermill equipped for liquid nitrogen injection into the grinding chamber. The mill was operated at 5800 rpm and had a 0.0156 inch screen.

The powder from this procedure was tableted as set forth in Example II.

EXAMPLE V 2 pounds of fondant sugar, ¼ oz. of salt, 10 oz. of finely powdered antacid mixture (FMA-11), 1 pound 2 oz. of melted shortening, 3½ oz. water, 6 drops of green food coloring and 23 drops of peppermint flavor were mixed together and rolled into dough of desired thickness. Pills were cut into tablets using a cookie cutter and the resulting tablets allowed to dry.

EXAMPLE VI 21 oz. of sucrose and 4.1 of salt were dissolved in 8 oz. of water. The solution was brought to a boil and kept boiling until a temperature of about 256° F. was reached. At this point the heated mass was cooled on a marble slab. 4 oz. of butter was melted and mixed with 1 oz. of cottonseed oil. 3½ oz. of finely powdered antacid mixture (designated FMA-11 and composed of a mixture of aluminum hydroxide and magnesium carbonate) was then dispersed throughout the liquid mixture using a Hobart mechanical mixer. The antacid and fat mixture was then folded into the cooled boiled sugar mass along with 17 drops of peppermint oil and 7 drops of green food coloring. This mass was then pulled until crystallization began to take place. At this point the mass was formed into ropes and cut into pillow shapes.

To demenstrate the "hardness" of the tablets made as in Example I, we subjected the tablets to tests on the Instron testing machine using a probe having a cone-shaped end with rounded end tip and measured the peak force needed to drive the probe 0.075 inches into the tablet at a speed of 0.5 inches per minute.

A critical element of such a test is the shape of the end of the probe which is pressed into the surface of the tablet. In our hardness tests, we used a probe having a blunt point resembling a half sphere with a diameter of 0.175 inches and this blunt tip was pressed slowly into the surface of the tablet at a rate of 0.5 inches per minute. The peak force necessary to move the tip to a depth of 0.075 inches was then taken as a measure of the hardness of the tablet.

We find that tablets made as set forth in Example I have a peak penetration force of less than 9 pounds whereas any other antacid tablet known to us and in commercial use today requires much higher force for this standard penetration under similar test conditions.

Table I contains data obtained by testing the improved tablets of this invention and comparing these with other antacid tablets known to the trade.

TABLE I

| Make of Tablet | Peak Force Required (lbs. per sq. in.) for Penetration .075 inches in Surface of Tablet |
|---|---|
| Tablet as prepared in Example I: Average of 40 samples from 8 lots | 3.5 |
| Mylanta II Average of 10 samples | 28.4 |
| Di-Gel Average of 10 samples | 23.8 |
| Maalox No. 2 Average of 7 samples | 34.7 |
| Tums Average of 6 samples | 15.2 |
| Alka 2 Average of 6 samples | 15.5 |

While our invention has been set forth and demonstrated in terms of certain embodiments, it must be understood that other embodiments may be utilized, and many changes and variations may be made both as to the formulation of the improved tablets and as to their process of manufacture all within the spirit of the invention and within the scope of the appended claims.

We claim:

1. In a process for preparing an antacid tablet in which an antacid ingredient, sugar and fat are combined to provide a powdered mixture, the step of feeding said mixture into a tableting machine while maintaining the plungers and dies of said machine at a temperature of from 110° to 125° F.

2. A process as set forth in claim 1 in which said temperature of said dies and plungers is maintained by heating the room in which said machine is contained to maintain said room at said temperature.

3. A process as set forth in claim 1 in which said temperature of said plungers and dies is maintained by placing said machine under a shroud and maintaining the temperature of the machine at about 110° to 125° F.

4. In a process for preparing an antacid tablet in which an antacid ingredient, sugar and fat are combined, the steps of mixing said fat in liquid form and said antacid with said sugar, cooling the mixture to a temperature below 40° F., and passing said cooled mixture through a mill to obtain a powdered mixture and forming said powdered mixture into tablets, by passing said powder mixture through a tableting machine while maintaining the the plungers and dies of said machine at a temperature of about 110° to 125° F.

5. A process as set forth in claim 1 in which said fat is contained in said mixture in an amount from 15 to 30%, said percentage being by weight based on the total weight of the tablet, said fat having a melting point of about 101° to 115° F.

* * * * *